(12) United States Patent
Jerome et al.

(10) Patent No.: US 7,537,937 B2
(45) Date of Patent: May 26, 2009

(54) LATERAL FLOW ASSAY DEVICE

(75) Inventors: Jeremy Jerome, Carlsbad, CA (US); Mark Daquipa, San Diego, CA (US); Bruce Jacono, Ramona, CA (US); Hans Boehringer, San Diego, CA (US)

(73) Assignee: Quidel Corporation, San Diego, CA (US)

( * ) Notice: Subject to any disclaimer, the term of this patent is extended or adjusted under 35 U.S.C. 154(b) by 0 days.

(21) Appl. No.: 11/757,270

(22) Filed: Jun. 1, 2007

(65) Prior Publication Data

US 2007/0281370 A1 Dec. 6, 2007

Related U.S. Application Data

(63) Continuation of application No. 10/461,157, filed on Jun. 12, 2003, now Pat. No. 7,226,793, which is a continuation of application No. 09/950,366, filed on Sep. 10, 2001, now Pat. No. 6,855,561.

(51) Int. Cl.
*G01N 33/53* (2006.01)

(52) U.S. Cl. .................. 436/518; 436/514; 436/169; 436/172; 436/175; 436/530; 436/807; 436/810; 436/823; 435/287.1; 435/287.2; 422/56; 422/58; 422/59; 422/60; 422/61

(58) Field of Classification Search ................ 436/514, 436/518, 169, 172, 175, 530, 807, 810, 823; 435/287.1, 287; 422/56–61
See application file for complete search history.

(56) References Cited

U.S. PATENT DOCUMENTS 3,992,158 A 11/1976 Przybylowicz et al.
4,275,149 A 6/1981 Litman et al.

(Continued)

FOREIGN PATENT DOCUMENTS

EP 0249418 A2 9/1987

(Continued)

OTHER PUBLICATIONS

Lindberg, "Plastic-Molding Processes", Chapter 10 in: *Processes and Materials of Manufacture*, Allyn and Bacon, Boston (1983) pp. 393-432.

*Primary Examiner*—Bao-Thuy L Nguyen
(74) *Attorney, Agent, or Firm*—Judy M. Mohr; King & Spalding LLP

(57) ABSTRACT

A test device and method for determining the presence or absence of an analyte in a fluid sample, the test device including a support bearing a mark thereon, and a matrix defining an axial flow path. In operation, an observation area in the test device becomes transparent, thereby allowing the user to view a mark that is present on a support that is disposed beneath the observation area. Typically, the mark on the underlying support is configured as a minus (−) sign. In the absence of analyte in the sample, the test device presents a negative result as a minus (−) signal. In the presence of analyte in the sample, however, the mark operates in concert with a perpendicular test line on the observation area to present a positive result as a plus (+) signal that is visible to the user.

10 Claims, 4 Drawing Sheets

U.S. PATENT DOCUMENTS

| | | | |
|---|---|---|---|
| 4,299,916 A | 11/1981 | Litman et al. | |
| 4,366,241 A | 12/1982 | Tom et al. | |
| 4,373,932 A | 2/1983 | Gribnau et al. | |
| 4,587,099 A | 5/1986 | Rothe et al. | |
| 4,632,901 A | 12/1986 | Valkirs et al. | |
| 4,695,554 A | 9/1987 | O'Connell et al. | |
| 4,806,311 A | 2/1989 | Greenquist | |
| 4,806,312 A | 2/1989 | Greenquist | |
| 4,824,640 A | 4/1989 | Hildenbrand et al. | |
| 4,863,875 A | 9/1989 | Bailey et al. | |
| 4,916,056 A | 4/1990 | Brown, III et al. | |
| 5,008,080 A * | 4/1991 | Brown et al. | 422/56 |
| 5,075,078 A | 12/1991 | Osikowicz et al. | |
| 5,110,550 A | 5/1992 | Schlipfenbacher et al. | |
| 5,145,789 A | 9/1992 | Corti et al. | |
| 5,160,701 A | 11/1992 | Brown et al. | |
| 5,223,220 A | 6/1993 | Fan et al. | |
| 5,338,513 A | 8/1994 | Schlipfenbacher et al. | |
| 5,401,667 A | 3/1995 | Koike | |
| 5,591,645 A | 1/1997 | Rosenstein | |
| 5,622,871 A | 4/1997 | May et al. | |
| 5,656,503 A | 8/1997 | May et al. | |
| 5,753,517 A * | 5/1998 | Brooks et al. | 436/514 |
| 5,985,675 A | 11/1999 | Charm et al. | |
| 6,046,058 A * | 4/2000 | Sun | 436/514 |
| 6,165,798 A | 12/2000 | Brooks | |
| 6,187,268 B1 | 2/2001 | Albarella et al. | |
| 6,284,198 B1 | 9/2001 | Kirollos et al. | |
| 6,316,205 B1 | 11/2001 | Guan et al. | |
| 7,297,502 B2 | 11/2007 | Gao et al. | |

FOREIGN PATENT DOCUMENTS

| | | |
|---|---|---|
| EP | 0258963 A2 | 3/1988 |
| EP | 353500 A2 | 7/1989 |
| EP | 0260965 A2 | 11/1992 |

* cited by examiner

LATERAL FLOW ASSAY DEVICE

CROSS-REFERENCES TO RELATED APPLICATIONS

This application is a continuation of U.S. application Ser. No. 10/461,157, filed Jun. 12, 2003, currently pending, which is a continuation of U.S. application Ser. No. 09/950,366, filed Sep. 10, 2001, which issued as U.S. Pat. No. 6,855,561 on Feb. 15, 2005.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK.

Not Applicable

BACKGROUND OF THE INVENTION

The present invention relates generally to devices and methods for detection of analytes in test samples. More specifically, the present invention provides solid phase test strip devices and methods that combine an internal indicator on the test strip with an external mark located on a support.

Various analytical procedures and devices are commonly employed in detection assays to determine the presence and/or amount of substance of interest or clinical significance which may be present in biological or non-biological fluids. Such substances are generally termed "analytes" and can include antibodies, antigens, drugs, or hormones.

The present invention includes lateral flow chromatography assay formats. Generally, these assays have an extended base layer on which a differentiation can be made between a sample application region and an evaluation region. In typical use, the sample is applied to the sample application region, flows along a liquid transport path which runs parallel to the base layer, and then flows into the evaluation region. A capture reagent is present in the evaluation region, and the captured analyte can be detected by a variety of protocols to detect visible moieties associated with the captured analyte. For example, the assay may produce a visual signal, such as color change, fluorescence, luminescence, and the like, when indicating the presence or absence of an analyte in a biological sample.

Optimally, such test devices will provide a characteristic signal when the analyte is present in a sample, and a different signal when the analyte is absent from a sample. Most typically, the test device will display a "plus" (+) signal in the presence of analyte, and a "minus" (−) signal in the absence of analyte. The plus/minus test result format has enjoyed enthusiastic customer response and wide commercial success.

Test devices of this kind are well known in the art, and play an important role in areas such as clinical chemistry. They are used by skilled clinicians and lay person alike. Thus, there is a strong impetus to provide devices that are simple and reliable. Desirably, the assays are single-step devices wherein the user need only apply the sample prior to viewing the result. Single-step devices obviate the necessity of performing complicated and time consuming processing steps that may introduce errors in the end result.

Examples of such assays include pregnancy tests, ovulation tests, various urine, saliva, spinal, and blood tests, as well as other clinical or diagnostic assays.

Test devices typically use materials that specifically bind with an analyte of interest. A homologous pair of specific binding pair members ("sbp members"), usually an immunological pair comprising a ligand and a receptor (antiligand), is involved, wherein one of the sbp members is labeled with a label that provides a detectable signal. The immunoassay methodology results in a distribution of the signal label between signal label bound in a complex of the sbp members and unbound signal label. The differentiation between bound and unbound signal label can be a result of physical separation of bound from unbound signal label or modulation of the detectable signal between bound and unbound signal label.

In developing an assay device, there are many considerations. One consideration is to provide substantial differentiation between the observed signal resulting from signal label when bound as compared to unbound. Another consideration is the ease with which the observed signal can be detected and serve to differentiate between the presence or absence of analyte of interest. Other factors include the precision with which the test devices must be manufactured. Therefore, in developing an assay that can be used by untrained personnel, such as assays to be performed in the home, medical offices and the like, the technique for performing the assay should be simple, and the method of manufacturing the assay should be straightforward.

Plus/Minus Assays

Of particular interest to the present invention are test devices of the type described in U.S. Pat. No. 5,145,789 to Corti et al., the disclosure of which is incorporated herein by reference. Corti et al. discuss a built-in positive control to indicate successful operation of a pregnancy test device. The positive control is envisaged as a horizontal tract that always stains, independent of the presence of hCG in the urine, and is described as an area on a membrane that contains immobilized hCG. Regardless of whether hCG is present in the biological sample, it is intended that during operation, the upstream mobile labeled hCG binding reagents will always bind to the immobilized hCG, thereby forming a horizontal line, or minus sign, in the reading area.

A similar approach for providing a minus sign in a test device is described in U.S. Pat. Nos. 4,916,056 and 5,008,080 to Brown, III et al., the disclosures of which are incorporated herein by reference. As illustrated, the positive control is formed by providing a binding substance within the test strip matrix, and is formed in the shape of a rectangular bar, or minus sign. The binding substance of the minus sign is intended to bind the labeled material regardless of the presence or absence of the analyte of interest in the test sample.

Another approach for providing a positive control in a test device is described in EP Patent Publication No. 0 249 418 to Graham, Jr., the disclosure of which is incorporated herein by reference. As described, the control zone has anti-human IgG or IgM immobilized thereon, for nonspecifically capturing human immunoglobulin ubiquitously present in all similar human aqueous samples. The immobilized antibody is intended to provide a signal in a "minus" pattern, regardless of the presence or absence of the analyte of interest in the test sample.

Osikowicz et al., in U.S. Pat. No. 5,075,078, describe yet another approach for providing a positive control in a plus/minus test device. The positive control is disposed on a test strip in a rectangular bar configuration. The control bar is oriented on the strip so that it lies neither perpendicular nor parallel to the direction of fluid flow, but rather lies at an intermediate orientation, i.e., at a 45 degree angle.

Still yet another approach for providing a positive control in a test device is provided in U.S. Pat. No. 5,401,667 to Koike. As described, the test device provides a plus/minus format, but considers alternative geometric symbols as well. A portion of the chromatographic medium is removed, or otherwise partially blocked, thereby affecting the flow path of the liquid. It is suggested that this modification enhances the signal of the device.

Wong et al., in EP Patent No. 0 260 965, describe another test device that utilizes the plus/minus format. Wong et al. discuss a multiple-step diagnostic assay with a horizontal positive control line sprayed onto a test membrane.

The previous methods discussed above accomplish the "appearance" of a minus sign (−) by placing an indicator (positive control) line perpendicular to the test line, directly onto the test strip. Typically, the control line develops with any sample flow, while the test line develops only with a positive sample flow. Thus, the previous assays involve a control mechanism inherent to the matrix membrane test strip, and require a specific manufacturing step to apply the control line to the strip.

Other previous devices display a printed minus sign positioned on the matrix and across the test line. These devices typically incorporate a positive control line downstream from, and parallel to, the test line. Such devices are limited as the test strips may present a line that is visible before the sample is added.

Previous methods are further disadvantaged as the additional manufacturing step involves a difficult placement procedure to orient the perpendicular line directly in the center of the viewing window. Whether the perpendicular line is a printed minus sign, or a reagent-based control line, this approach is particularly ill suited for certain matrix construction procedures, including web processing methods that involve a continuous flow or continuous roll application approach.

Therefore, it would be desirable to provide a test device that does not require this extra processing step of depositing a perpendicular line onto the test strip, or does not leave a line that is visible before the sample is added to the device. This invention fulfills these and other needs.

Transparent Membranes

The use of transparent test strips in diagnostic assays is known in the art. In U.S. Pat. No. 4,824,640, Hildebrand et al. discuss a transparent reagent carrier layer suitable for evaluation by transmission photometry. As described, the transparent nature of the film of plastic provides a suitable carrier material as compared to opaque films.

The use of a transparent test strip is also discussed in U.S. Pat. No. 5,110,550 to Schlipfenbacher et al. As described, this test device includes a white non-transparent covering layer situated above a color-forming layer. During operation of the test device, the covering layer becomes transparent in the moist state. Through the transparent covering layer, the user is then able to observe any reaction occurring in the color-forming layer below.

The use of a clearing agent in an immunochromatographic assay is discussed in U.S. Pat. No. 6,165,798 to Brooks. As described, the test strip membrane is rendered transparent by wetting the membrane with a clearing agent, thus reducing the amount of light scattered by the membrane fibers.

In U.S. Pat. No. 6,187,268, Albarella et al. describe a transparent flow through membrane for use in test devices, but do not suggest a control feature to indicate a positive or negative test result. The membrane described in Albarella et al. is not configured to become transparent only when wet. The membrane is transparent whether wet or dry.

While conceivably workable in some circumstances, the previous detection systems that employ transparent membranes are of limited utility. There is no teaching or suggestion in current art for a test device with a transparent membrane that utilizes a control feature to indicate a positive or negative test result as provided by a mark on the underlying support.

In view of the foregoing, there remains a need in the art for a simple, efficient method for adding a positive control to a solid phase assay that does not require the manufacturing step of fixing a positive control binding member to the assay test strip, and that does not leave a substantially visible before the sample is added to the device. It would further be desirable to achieve improved test device formats that incorporate transparent membranes as part of a control or display feature.

Additionally, the assay of the present invention should overcome the disadvantages described above in connection with the previous test device systems.

BRIEF SUMMARY OF THE INVENTION

The present invention includes devices, methods, and kits for visually detecting the presence or absence of an analyte in a sample. For example, the present invention provides a test device for determining the presence or absence of an analyte in a fluid sample. The test device comprises a flow matrix disposed above a support. The matrix defines an axial flow path, and typically contains three zones.

First, a sample receiving zone is located at an upstream end of the flow path. The test sample suspected of containing an analyte of interest is applied to the sample receiving zone. Second, a label zone is located on the flow path downstream from the sample receiving zone. As the test sample flows through the label zone, it contacts a mobile labeled reagent. This labeled reagent is specific for, and binds to, the analyte of interest. Third, an observation area is located at the downstream end of the flow path. A capture zone is situated in the area, and contains immobilized capture reagents that are specific for, and bind with, the analyte of interest. Generally, the binding is achieved by either a direct or an indirect binding approach. Optionally, an absorbent zone is disposed downstream of the observation area.

The sample fluid travels from the sample receiving zone, through the label zone, and then across the observation area and capture zone. The observation area, now moistened from the sample fluid, becomes transparent. The user can then view a mark displayed on the underlying support.

The present invention is simple, effective, and solves the problems of previous devices and methods, by providing a test device with a transparent membrane and an underlying support that bears a mark.

This invention utilizes a property of nitrocellulose, or a similar membrane, in that it becomes transparent when it is wet. By placing a detectable line or symbol directly underneath the nitrocellulose capture zone, that marking will be mostly invisible until a liquid sample is added. When the membrane becomes wet, the markings underneath it become instantaneously visible and appear to be a part of the displayed results.

The invention described herein allows the mark to be placed in a precisely controlled location within the window and can be printed directly on the plastic housing or on an intermediate member disposed between the housing and the test strip. This allows for the actual test strip to be processed continuously in that there is no need to manufacture a control line or minus symbol that is perpendicular to the processing flow. This feature is particularly desirable in web processing procedures.

The invention does not require any chemical interaction between a label component and a capture component to produce the appearance of a line or symbol in any shape or color. The invention imparts a very distinct look and operability characteristic to a lateral flow device.

The present invention achieves the "appearance" of a minus sign (−) by placing an indicator mark perpendicular to the test line, directly on the underlying support. The mark typically manifests with any sample flow, while the test line develops only with a positive sample flow. A further advantage of the present invention is the avoidance of a line that is substantially visible before the sample is added to the device.

Other objects and advantages will become apparent from the following detailed description taken in conjunction with the drawings in which:

DETAILED DESCRIPTION OF THE INVENTION

Figure 1:
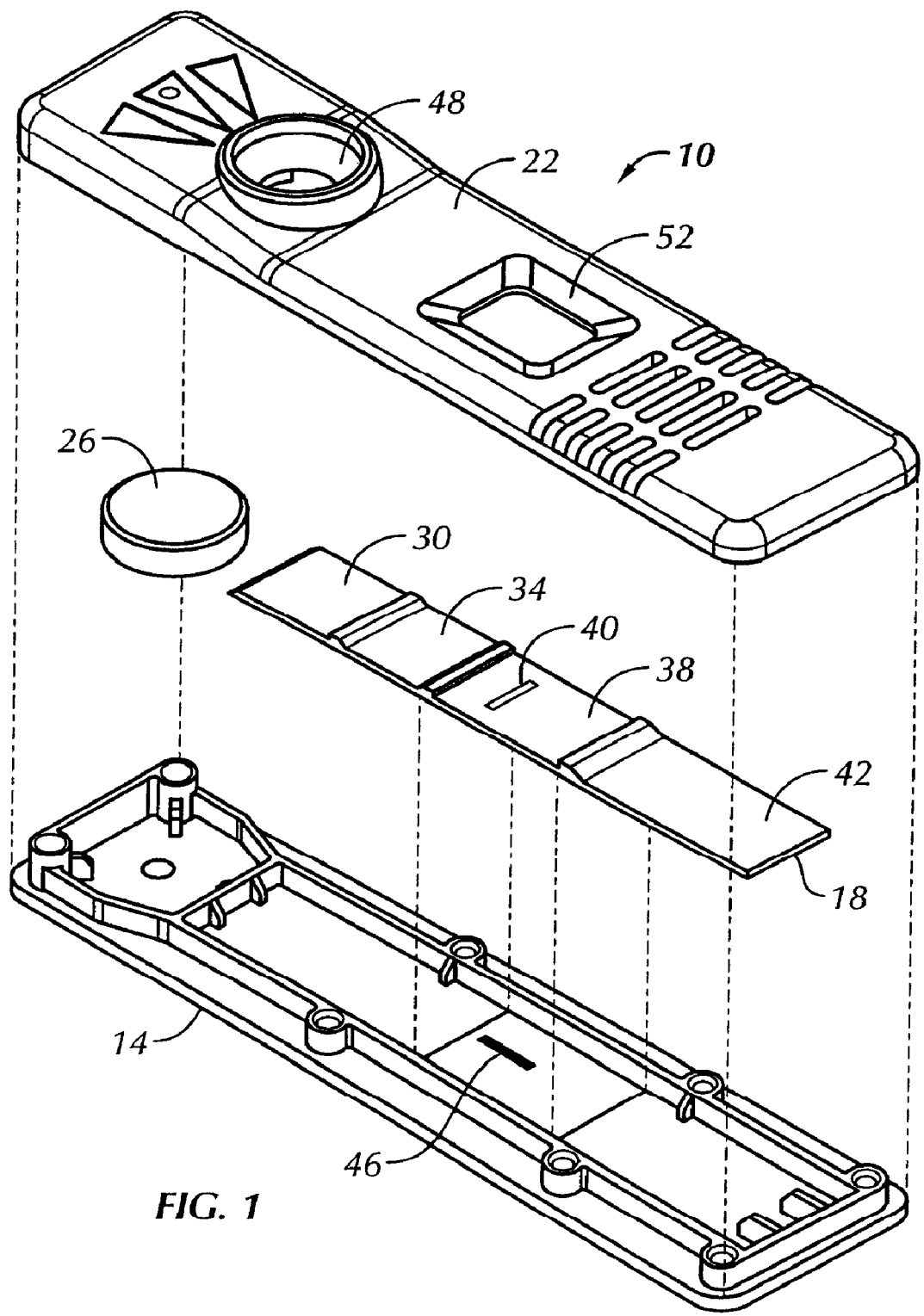
FIG. 1 is an exploded perspective view of a test device of the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

In describing the various aspects of the present invention, a number of terms will be generally defined or abbreviated as follows.

Definitions

"Fluid sample" refers to a material suspected of containing the analyte of interest. The fluid sample can be used as obtained directly from the source or following a pretreatment so as to modify its character. Such samples can include human, animal or man-made samples. The sample can be prepared in any convenient medium which does not interfere with the assay. Typically, the sample is an aqueous solution or biological fluid as described in more detail below.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte. The selection and pretreatment of biological, industrial, and environmental samples prior to testing is well known in the art and need not be described further.

"Specific pair binding member" refers to a member of a specific binding pair, i.e., two different molecules wherein one of the molecules specifically binds with the second molecule through chemical or physical means. The two molecules are related in the sense that their binding with each other is such that they are capable of distinguishing their binding partner from other assay constituents having similar characteristics. The members of the specific binding pair are referred to as ligand and receptor (antiligand), sbp member and sbp partner, and the like. A molecule may also be a sbp member for an aggregation of molecules; for example an antibody raised against an immune complex of a second antibody and its corresponding antigen may be considered to be an sbp member for the immune complex.

In addition to antigen and antibody specific binding pair members, other specific binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogs of the original specific binding member, for example an analyte-analog or a specific binding member made by recombinant techniques or molecular engineering.

An sbp member is analogous to another sbp member if they are both capable of binding to another identical complementary sbp member. Such an sbp member may, for example, be either a ligand or a receptor that has been modified by the replacement of at least one hydrogen atom by a group to provide, for example, a labeled ligand or labeled receptor. The sbp members can be analogous to or complementary to the analyte or to an sbp member that is complementary to the analyte.

If the specific binding member is an immunoreactant it can be, for example, an antibody, antigen, hapten, or complex thereof. If an antibody is used, it can be a monoclonal or polyclonal antibody, a recombinant protein or antibody, a chimeric antibody, a mixture(s) or fragment(s) thereof, as well as a mixture of an antibody and other specific binding members. The details of the preparation of such antibodies and their suitability for use as specific binding members are well-known to those skilled in the art.

When an immunoreactive specific binding member is attached to the chromatographic material of the present invention, the device is referred to as an "immunochromatograph", and the corresponding method of analysis is referred to as "immunochromatography". Immunochromatography, as used herein, encompasses both sandwich and competitive immunoassay techniques.

"Ligand" refers to any compound for which a receptor naturally exists or can be prepared.

"Receptor" refers to any compound or composition capable of recognizing a particular spatial or polar orientation of a molecule, e.g., epitopic or determinant site. Illustrative receptors include: antibodies, enzymes, thyroxine binding globulin, intrinsic factor, lectins, nucleic acids, protein A, complement, complement Clq, and the like. Receptors are also referred to as antiligands.

"Antigen" shall mean any compound capable of binding to an antibody, or against which antibodies can be raised.

"Antibody" refers to a polypeptide substantially encoded by an immunoglobulin gene or immunoglobulin genes, or fragments thereof. The recognized immunoglobulin genes include the kappa, lambda, alpha, gamma, delta, epsilon, and mu constant regions, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, an antibody is an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof. Fragments thereof may include Fab, Fv and F(ab')2, Fab', and the like. Antibodies may also include chimeric antibodies made by recombinant methods.

"Analyte" or "analyte of interest" refers to the compound or composition to be detected or measured and which has at least one epitope or binding site. The analyte can be any substance for which there exists a naturally occurring analyte specific binding member or for which an analyte-specific binding member can be prepared. e.g., carbohydrate and lectin, hormone and receptor, complementary nucleic acids, and the like. Further, possible analytes include virtually any compound, composition, aggregation, or other substance which may be immunologically detected. That is, the analyte, or portion thereof, will be antigenic or haptenic having at least one determinant site, or will be a member of a naturally-occurring binding pair.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof. A non-exhaustive list of exemplary analytes is set forth in U.S. Pat. No. 4,366,241, at column 19, line 7 through column 26, line 42, the disclosure of which is incorporated herein by reference. Further descriptions and listings of representative analytes are found in U.S. Pat. Nos. 4,299,916; 4,275,149; and 4,806, 311, all incorporated herein by reference.

"Label reagent" refers to a substance comprising a detectable label attached with a specific binding member. The attachment may be covalent or non-covalent binding, but the method of attachment is not critical to the present invention. The label allows the label reagent to produce a detectable signal that is related to the presence of analyte in the fluid sample. The specific binding member component of the label reagent is selected to directly bind to the analyte or to indirectly bind the analyte by means of an ancillary specific binding member, which is described in greater detail hereinafter. The label reagent can be incorporated into the test device at a site upstream from the capture zone, it can be combined with the fluid sample to form a fluid solution, it can be added to the test strip or device separately from the test sample, or it can be predeposited or reversibly immobilized at the capture zone. In addition, the specific binding member may be labeled before or during the performance of the assay by means of a suitable attachment method.

"Label" refers to any substance which is capable of producing a signal that is detectable by visual or instrumental means. Various labels suitable for use in the present invention include labels which produce signals through either chemical or physical means. Such labels can include enzymes and substrates, chromogens, catalysts, fluorescent compounds, chemiluminescent compounds, and radioactive labels. Other suitable labels include colloidal metallic particles such as gold, colloidal non-metallic particles such as selenium or tellurium, dyed or colored particles such as a dyed plastic or a stained microorganism, organic polymer latex particles and liposomes, colored beads, polymer microcapsules, sacs, erythrocytes, erythrocyte ghosts, or other vesicles containing directly visible substances, and the like. Typically, a visually detectable label is used as the label component of the label reagent, thereby providing for the direct visual or instrumental readout of the presence or amount of the analyte in the test sample without the need for additional signal producing components at the detection sites.

The selection of a particular label is not critical to the present invention, but the label will be capable of generating a detectable signal either by itself, or be instrumentally detectable, or be detectable in conjunction with one or more additional signal producing components, such as an enzyme/substrate signal producing system. A variety of different label reagents can be formed by varying either the label or the specific binding member component of the label reagent; it will be appreciated by one skilled in the art that the choice involves consideration of the analyte to be detected and the desired means of detection. As discussed below, a label may also be incorporated used in a control system for the assay.

For example, one or more signal producing components can be reacted with the label to generate a detectable signal. If the label is an enzyme, then amplification of the detectable signal is obtained by reacting the enzyme with one or more substrates or additional enzymes and substrates to produce a detectable reaction product.

In an alternative signal producing system, the label can be a fluorescent compound where no enzymatic manipulation of the label is required to produce the detectable signal. Fluorescent molecules such as fluorescein, phycobiliprotein, rhodamine and their derivatives and analogs are suitable for use as labels in such a system.

The use of dyes for staining biological materials, such as proteins, carbohydrates, nucleic acids, and whole organisms is documented in the literature. It is known that certain dyes stain particular materials preferentially based on compatible chemistries of dye and ligand. For example, Coomassie Blue and Methylene Blue for proteins, periodic acid-Schiff's reagent for carbohydrates, Crystal Violet, Safranin O, and Trypan Blue for whole cell stains, ethidium bromide and Acridine Orange for nucleic acid staining, and fluorescent stains such as rhodamine and Calcofluor White for detection by fluorescent microscopy. Further examples of labels can be found in, at least, U.S. Pat. Nos. 4,695,554; 4,863,875; 4,373, 932; and 4,366,241, all incorporated herein by reference.

"Signal producing component" refers to any substance capable of reacting with another assay reagent or with the analyte to produce a reaction product or signal that indicates the presence of the analyte and that is detectable by visual or instrumental means. "Signal production system", as used herein, refers to the group of assay reagents that are needed to produce the desired reaction product or signal.

"Ancillary specific binding member" refers to any member of a specific binding pair which is used in the assay in addition to the specific binding members of the conjugate or capture reagent. One or more ancillary specific binding members can be used in an assay. For example, an ancillary specific binding member can be capable of binding the conjugate with the analyte of interest, in instances where the analyte itself could not directly attach to the conjugate. Optionally, the ancillary binding member may be capable of binding the analyte with the capture reagent, in instances where the analyte itself could not directly attach to the capture reagent. The ancillary specific binding member can be incorporated into the assay device or it can be added to the device as a separate reagent solution.

"Solid phase" refers to any solid material to which analyte, analyte complexes, or assay reagents become bound and which can be separated from unreacted assay reagents, test sample, or test solutions. For example, the solid phase may involve beads, magnetic particles, latex particles, test tubes, microtiter plates, or any other solid material. Generally, the solid phase is any suitable chromatographic, bibulous, porous, isotropic, or capillary material, hereinafter referred to as porous material, which forms the basis of the test device.

"Capture reagent" refers to a specific binding member that is attached within or upon a portion of the solid phase to form a "capture zone". The method of attachment is not critical to the present invention. The capture reagent is selected to bind the analyte, the conjugate, or a complex thereof.

"Ancillary material" shall mean any material that may be employed in an assay in accordance with the present invention. For example, buffer will normally be present in the labeling means, the neutralization means, as well as stabilizers for the assay medium and assay components. Frequently, in addition to these additives, additional protein, such as albumin, or surfactant, non-ionic or ionic, binding enhancer, for example, polyalkylene glycol, or the like, may be present, including free antibody, analyte analog, or other unrelated ligand, for the purpose of removing or adding material or to modify the amount, position, partitioning, or appearance of the analyte or other compound used in the invention.

Introduction

The present invention relates generally to devices and methods for detection of analytes in test samples. More specifically, the present invention provides solid phase test strip devices and methods that combine an internal indicator on the test strip with an external mark located on a support.

Test Device

In a first aspect, the present invention provides a test device for determining the presence or absence of an analyte in a fluid sample. The test device includes a support bearing a mark thereon, and a matrix defining an axial flow path. Typically, the matrix further includes a sample receiving zone, a label zone, and an observation area that contains a capture zone. In a related embodiment, the matrix further includes an absorbent zone disposed downstream of the observation area.

In a preferred embodiment, the sample receiving zone accepts a fluid sample that may contain an analyte of interest. A label zone is located downstream of the sample receiving zone, and contains a mobile label reagent that recognizes the analyte of interest. Further, an observation area is disposed downstream of from the label zone, and contains an immobilized capture reagent that binds to the analyte of interest. Thus, as the fluid sample flows along the matrix, the analyte of interest will first bind with the mobile label reagent in the label zone, and then bind to the immobile capture reagent in the capture zone of the observation area. The observation area is made of a material that is opaque in a dry state and transparent in a moist state. Thus, the mark on the support is visible through the observation area when the observation area is in the moist state.

In another preferred embodiment, the fluid sample flows along a flow path running from the sample receiving zone (upstream), through the label zone (midstream), and then to the observation area (downstream). Optionally, the fluid may thereafter flow to the absorbent zone.

In a preferred embodiment, the sample receiving zone is made of an absorbent application pad. Suitable materials for manufacturing absorbent application pads include, but are not limited to, hydrophilic polyethylene materials or pads, glass fiber filter paper or pads, desiccated paper, paper pulp, fabric, and the like. In a related embodiment, the sample receiving zone is constructed from any material that absorbs water.

In a preferred embodiment, the absorbent application pad is made of any material from which the fluid sample can pass to the label zone. Further, the absorbent application pad may be constructed to act as a filter for cellular components, hormones, particulate, and other certain substances that may occur in the fluid sample. Application pad materials suitable for use by the present invention also include those application pad materials disclosed in U.S. Pat. No. 5,075,078, incorporated herein by reference.

In yet another preferred embodiment, the absorbent application pad may incorporate other reagents such as ancillary specific binding members, fluid sample pretreatment reagents, and signal producing reagents.

In a particularly preferred embodiment, the analyte of interest is from the group including heartworm antigens, hCG (human chorionic gonadotropin), streptococcus A, and other bacterial antigens.

In another preferred embodiment, the test device is configured to perform an immunological analysis process. In yet another embodiment, the liquid transport along the matrix is based upon capillary action, whereby the liquid transport path can be formed not only by one or more layers of absorbent material, for example paper or fleece, but also by a gap which is sucked full by capillary action.

In a preferred embodiment, the label zone is capable of non-bibulous lateral flow. By "non-bibulous lateral flow" is meant liquid flow in which all of the dissolved or dispersed components of the liquid are carried at substantially equal rates and with relatively unimpaired flow laterally through the membrane, as opposed to preferential retention of one or more components as would occur, e.g., in materials capable of adsorbing or imbibing one or more components.

In a further preferred embodiment, the label zone is made of a typical non-bibulous material such as high density polyethylene sheet material manufactured by Porex Technologies Corp. of Fairburn, Ga., USA. The sheet material has an open pore structure with a typical density, at 40% void volume, of 0.57 gm/cc and an average pore diameter of 1 to 250 micrometers, the average generally being from 3 to 100 micrometers. The optimum pore diameter for the membrane for use in the invention is about 10 to about 50 μm. The membranes typically are from about 1 mil to about 15 mils in thickness, typically in the range of from 5 or 10 mils, but may be up to 200 mils and thicker. The membrane may be backed by a generally water impervious layer, such as mylar. When employed, the backing is generally fastened to the membrane by an adhesive, such as 3M 444 double-sided adhesive tape. Typically, a water impervious backing is used for membranes of low thickness. A wide variety of polymers may be used provided that they do not bind nonspecifically to the assay components and do not interfere with flow of the sample. Illustrative polymers include polyethylene, polypropylene, polystyrene and the like. Alternatively, the membrane may be self supporting. Other non-bibulous membranes, such as polyvinyl chloride, polyvinyl acetate, copolymers of vinyl acetate and vinyl chloride, polyamide, polycarbonate, polystyrene, and the like, can also be used.

In yet another preferred embodiment, the label zone is made of a material such as untreated paper, cellulose blends, nitrocellulose, polyester, an acrylonitrile copolymer, and the like. The label zone may be constructed to provide either bibulous or non-bibulous flow. In an especially preferred embodiment, the label zone is made of a nonwoven fabric such as Rayon or glass fiber. Other label zone materials suitable for use by the present invention include those chromatographic materials disclosed in U.S. Pat. No. 5,075,078, which is herein incorporated by reference. In a preferred embodiment, the label zone material may be treated with labeled solution that includes blocking and stabilizing agents. Blocking agents include bovine serum albumin (BSA), methylated BSA, casein, nonfat dry milk. Stabilizing agents are readily available and well known in the art, and may be used, for example, to stabilize colored labels.

In all of the above, employment of the selected blocking and stabilizing agents together with colored moieties in the labeling zone followed by the immobilization of the blocking and stabilizing agents on the support (by, e.g., a freeze-drying process, or a forced air heat drying process) is of utmost importance for improved performance of the device. It is well known that visible moieties, especially particles, aggregate upon air-drying and do not readily rehydrate in contact with a liquid sample. Therefore, absent conversion to the nonbibulous surface, instead of being transported to the capture zone with the sample, the visible moieties will remain trapped in the labeling zone.

In a particularly preferred embodiment, the observation area will be made of a material that is opaque when in a dry state, and transparent when in a moistened state, examples of which include nitrocellulose, nylon, and hydrophilic polyvinylidene difluoride (PVDF). Hydrophilic polyvinylidene difluoride (PVDF) is commercially available form the firm Millipore, Bedford, U.S.A. under trademark Immobilon AV. However, on the basis of the present description, the expert can also select other materials and especially synthetic material membranes which fulfill the above-mentioned conditions. It is believed that the refractive index of the synthetic material is of major influence to this characteristic. It is to be assumed that porous materials, the refractive index of which is close to that of the sample liquid, have the property of becoming transparent in a moist state.

In a particularly preferred embodiment, the observation area is a nitrocellulose web assembly made of Millipore nitrocellulose roll laminated to a clear Mylar backing. In another embodiment, the observation area is made of nylon.

Those skilled in the art will appreciate that various methods could be used to test the desired property of the observation area, and whether it is sufficiently opaque in the dry state, and sufficiently transparent in the moist state. For example, one could put a mark on a piece of plastic, and then place the test strip on top of the plastic and visually determine if it is opaque or transparent. Other methods include the use of scanner devices, or other means for determining optical density of the apparent line.

The artisan will appreciate the whole of the observation area, or only a portion thereof, may become transparent when moistened. In either embodiment, the portion of the observation area that is disposed above the mark should become transparent when moistened. In a related embodiment, the observation area will contain one or more distinct areas that are opaque in the dry state, and transparent in the moist state.

In a preferred embodiment, the capture zone may be constructed from any of the materials as listed above for the observation zone. In a particularly preferred embodiment, the capture zone is made of the same material as the observation zone. The artisan will recognize that the present invention envisages a test device with one or more capture zones.

Further embodiments include capture zones that include microporous materials made from nitrocellulose, by which term is meant any nitric acid ester of cellulose. Thus suitable materials may include nitrocellulose in combination with carboxylic acid esters of cellulose. The pore size of nitrocellulose membranes may vary widely, but is preferably within 5 to 20 microns, preferably 8 to 15 microns. To provide non-bibulous flow, these materials may be treated with blocking agents that can block the forces which account for the bibulous nature of bibulous membranes. Suitable blocking agents include bovine serum albumin, methylated bovine serum albumin, whole animal serum, casein, and non-fat dry milk.

In a preferred embodiment, the observation area further includes a procedural control line, to verify that the sample flow is as expected. The control line is a spatially distinct region that includes an immobilized binding member which reacts with a labeled reagent. In a preferred embodiment, the procedural control line contains an authentic sample of the analyte of interest, or a fragment thereof. In another preferred embodiment, the control line contains antibody that is specific for, or otherwise provides for the immobilization of, the labeled reagent. In operation, a labeled reagent binds to the control line, even when the analyte of interest is absent from the test sample.

In a related embodiment, a control conjugate is introduced into the flow sample upstream from the control line. For example, the control conjugate may be added to the fluid sample before the sample is applied to the assay device. Alternatively, the control conjugate may be diffusively bound in the sample receiving zone, or in the label zone.

In a preferred embodiment, the control conjugate includes a control label and a control reagent. Typically, a control reagent is chosen to be different from the reagent that is recognized by the capture reagent. Further, the control agent is generally not specific for the analyte. In a preferred embodiment, the control reagent binds to a control capture partner that is immobilized on the procedural control line. Thus the control conjugate is directly detected in the control line.

In yet another embodiment, the detectable control label is the same label used for the label reagent. In a preferred embodiment, the control label is different from the test label, so that the user can more easily determine the results of the assay. In a particularly preferred embodiment, the control label and the test label include colored beads, where the control and test beads are of different colors.

In a preferred embodiment, the control label includes streptavidin, and the control capture partner includes biotin, which couples to the avidin specifically. In a particularly preferred embodiment, the control label includes biotin, and the control capture partner includes streptavidin. The artisan will appreciate that other "irrelevant" binding pairs can also be used-such as antigen/antibody reactions unrelated to analyte.

The use of a control line is helpful in that appearance of a signal in the control line indicates the time at which the test result can be read, even for a negative result. Thus, when the expected signal appears in the control line, the presence or absence of a signal in the capture zone can be noted.

In another preferred embodiment, the matrix may further incorporate an absorbent zone. The absorbent zone can act to increase the amount of fluid sample that travels through the capture zone.

In this embodiment, the absorbent zone is located downstream from the capture zone and can be a means for removing excess sample and free label other than the analyte of interest from the matrix of the device. Generally, the absorbent zone will consist of an absorbent material such as filter paper, a glass fiber filter, or the like.

In a preferred embodiment, the device may also contain an end of assay control zone indicator. The control zone indicator may consist of a pH indicating reagent (such as bromocresol green) impregnated in the absorbent zone or at a location downstream of the capture zone. Upon contact with the sample, a pH change occurs in the processed matrix. This pH shift converts the pH indicator to a different color (for instance, bromocresol green may be converted from yellow to blue) which is seen in an observation window over the control zone. This technology may also serve as an internal assay control.

In a related embodiment, the end of assay control zone may be constructed by applying a line of soluble ink on the capture zone (at the interface with the absorbent zone). The liquid front moving through the capture zone will solubilize the ink and transfer it into the absorbent. The resulting color change will be seen in an observation window above the absorbent zone, signifying end of assay.

In a preferred embodiment, the capture reagent binds with the analyte for the completion of a sandwich complex. The capture reagent can be chosen to directly bind the analyte or indirectly bind the analyte by binding with an ancillary specific binding member which is bound to the analyte. In addition, the capture reagent may be immobilized on the solid phase before or during the performance of the assay by means of any suitable attachment method. Typically, the capture site of the present invention is a delimited or defined portion of the solid phase such that the specific binding reaction of the capture reagent and analyte is localized or concentrated in a limited site, thereby facilitating the detection of label that is immobilized at the capture site in contrast to other portions of the solid phase. In a related embodiment, the capture reagent can be applied to the solid phase by dipping, inscribing with a pen, dispensing through a capillary tube, or through the use of reagent jet-printing or other techniques. In addition, the capture zone can be marked, for example with a dye, such that the position of the capture zone upon the solid phase can be visually or instrumentally determined even when there is no label immobilized at the site.

Those of skill in the art will recognize that a variety of direct and indirect assay formats may be employed in the present invention. In a preferred embodiment, a direct assay format is used. Direct assays are exemplified by those that detect the presence of an antigen in a sample, as well as those that detect the presence of an antibody in a sample. A direct assay that detects the presence or absence of an antigen in a sample generally includes a label zone that contains at least one antibody label reagent that is specific for the antigen. In a preferred embodiment, the antibody is coated on colored beads. Likewise, a direct assay that detects the presence or absence of an antigen in a sample generally includes a label zone that contains at least one antigen that is reactive with an antibody-analyte of interest. In this embodiment, the antigen is coated on colored beads.

In a preferred embodiment, the result displayed by the test device incorporates a symbol provided by the mark on the bottom support. Due to the transparent nature of the observation area, the mark on the support is detectable through the moistened observation area. Thus, the shape of the mark will be displayed regardless of whether the analyte of interest is or is not present in the fluid sample. Typically, the shape of the mark provides a first symbol to represent a negative result. In a related embodiment, the symbol provided by the mark on the support is a minus (−) symbol. In a particularly preferred embodiment, the mark will be visible to the unaided eye, although those of skill in the art will appreciate that a variety of detection approaches may be employed. In another preferred embodiment, the mark will be blue or red, or any color which provides contrast with the surrounding area, which is typically a lighter color, such as white.

In a preferred embodiment, the mark on the support will operate in concert with a symbol provided by the capture zone. When the desired analyte is present in the fluid sample, label is collected at the capture zone. The shape of the labeled capture zone is such that, in combination with the mark, a second symbol is provided representing a positive result. In a related embodiment, the symbol presented by this combination is a plus (+) symbol.

In yet another preferred embodiment, the capture zone has a shape such that, independent of any symbol provided by that mark on the substrate, labeled reagent at the capture zone will form a second symbol to represent a positive test result.

In a preferred embodiment, the mark on the support is oriented so that the longitudinal axis of the mark is aligned with the direction of the sample flow, while the longitudinal axis of the capture zone is perpendicular to the direction of the sample flow. In a related embodiment, these axes may be at oblique angles to the sample flow. In yet another related embodiment, these axes may be oriented at any angle to the sample flow, so long as the axis of the mark and the axis of the capture zone are substantially perpendicular to each other.

In another preferred embodiment, the mark on the support includes a shape such that, in the presence or absence of the analyte of interest in the fluid sample, a logo is displayed in the observation area. In a related embodiment, the marked support provides one or more predefined symbols to be displayed when the observation area is moistened. These symbols may be read in connection with, or independent from, any signal that may be provided by the capture zone.

In yet another embodiment, the mark may be displayed below the capture zone, but not necessarily on the bottom support. For example, the mark may be contained on the Mylar strip underlying the nitrocellulose matrix membrane. Alternatively, the mark may be contained on an intermediate member disposed between the test strip and the bottom support. In a preferred embodiment, the intermediate member is a plastic strip displaying the mark. The member may or may not be affixed to either the test strip or the bottom support. In a preferred embodiment, the intermediate member is configured to remain in place once the test apparatus is constructed. In a related embodiment, the mark is applied, for example, by an embossing, printing, or stamping technique.

In still another preferred embodiment, the observation area includes a negative control area. The purpose of this control area is to alert the user that the test device is not working properly. In a preferred embodiment, the negative control is that part of the observation area outside of the capture zone, and does not include any part of the observation area located directly above the mark on the support. When working properly, no signal or mark should be visible in the negative control area.

In a preferred embodiment, the test device includes a hollow casing or housing having an application aperture and an observation port. In this embodiment, the flow matrix is contained within the hollow casing, and the fluid sample is added to the matrix through the aperture, which is an opening located in an upstream location on the housing.

Typically, the aperture is located above the sample application pad. In a related embodiment, an aperture may be disposed in any location above the matrix that would provide for facile addition of fluid sample or reagent to the matrix.

To detect the result, the observation area may be examined through the port. The artisan will appreciate that an observation port may be disposed in any location above the matrix that would provide for the detection of a signal event, whether the signal comes from the observation area, the absorbent zone, or elsewhere. In a preferred embodiment, the port is located above the observation area. Generally, the observation port is open, or the port may be covered by a transparent covering such as glass or plastic.

From the foregoing, it is appreciated that the outer casing or housing of the device may take various forms. Typically, it will include an elongate casing and may have a plurality of interfitting parts. In a particularly preferred embodiment, the housing includes a top cover and a bottom support. In a preferred embodiment, the bottom support displays a mark thereon, and in a related embodiment, the top cover contains an application aperture and an observation port. In another embodiment, the housing may also contain dividers between the matrix strips to inhibit flow of fluid sample between strips.

In a preferred embodiment, the housing is made of moisture impervious solid material, for example, a plastic material. It is contemplated that a variety of commercially available plastics, including, but not limited to, vinyl, nylon, polyvinyl chloride, polypropylene, polystyrene, polyethylene, polycarbonates, polysulfanes, polyesters, urethanes, and epoxies maybe used to construct a housing. The housing may be prepared by conventional methodologies, such as standard molding technologies that are well known and used in the art. The housing may be produced by molding technologies which include, but are not limited to, injection molding, compression molding, transfer molding, blow molding, extrusion molding, foam molding, and thermoform molding. The aforementioned molding technologies are well known in the art and so are not discussed in detail herein. See for example, Processes And Materials Of Manufacture, Third Edition, R. A. Lindsberg (1983) Allyn and Baron pp. 393-431.

It will be appreciated by one skilled in the art that a test strip device can be made of more than one material (e.g., different zones or sites can be made of different materials) and a flow-through device can have more than one layer, wherein different layers can be made of different materials, so long as the multiple materials or layers are in fluid-flow contact with one another thereby enabling the passage of test sample between the materials or layers. Fluid-flow contact permits the passage of at least some components of the test sample between the zones or layers of the device. Fluid-flow is preferably uniform along the contact interface between the different zones or layers. The present invention further provides for different reagents disposed on different materials, and different reagents disposed on different zones. For example, the specific binding member contained on a certain material in the label zone may or may not be the same binding member that is contained on a different material in the capture zone.

In further preferred embodiments, the test device of the present invention can have many configurations, several of which are dependent upon the material chosen for the solid phase. For example, the test device can include a solid phase material configured for use in a layered flow-through assay device, a chromatographic column, a dipstick or a test strip.

In a second aspect, the present invention provides a method for determining the presence or absence of an analyte in a fluid sample. The assay method includes providing a test device as described above, and administering a fluid sample to the test device. By inspecting the observation area of the test device, the user is able to determine whether the fluid sample contains the analyte of interest. Typically, this is accomplished by observing either a plus (+) or minus (−) signal in the observation area.

In a third aspect, the present invention provides a kit for determining the presence or absence of an analyte in a fluid sample. The assay kit of the present invention will include containers for holding any necessary reagent, test membrane, sample applicator, filter, and the like, as well as instructions which set forth a protocol for practicing the method of use as described above. Typically, the components of the kit will be present in a suitable package containing sufficient components for performing one or more assays.

The present invention is particularly suitable for a test device as shown in the accompanying drawings, and described in detail as follows. It is understood that the drawings are provided for purposes of illustration and not meant limit the scope of the present invention.

FIG. 1 shows a first embodiment of a test device 10 constructed in accordance with the teachings of the present invention.

Test device 10 has a bottom support 14, a flow matrix 18, a top cover 22, and a desiccant 26. In its longitudinal direction, matrix 18 can be subdivided into a sample application zone 30, a label zone 34, an observation area 38, and an absorbent zone 42.

The bottom support further includes a mark 46 thereon. The mark is disposed beneath observation area 38. The sample application zone is located at an upstream location on matrix 18, and is configured to receive the fluid sample. Label zone 34 is located downstream of application zone 30, and contains label reagent. The observation area is located downstream of the label zone, and includes a capture zone 40 that contains capture reagent. Absorbent pad 42 is located downstream of observation area 38.

Top cover 22 has an application aperture 48 disposed above the sample application pad, and an observation port 52 disposed above the observation area. In cooperation, the top cover and the bottom support are configured to provide a housing for matrix 18 and desiccant 26. As shown, the desiccant is typically positioned separately from the matrix.

Prior to use, when in the dry state, the observation area is opaque, and thus no signal is manifested through the observation port.

Figure 2:
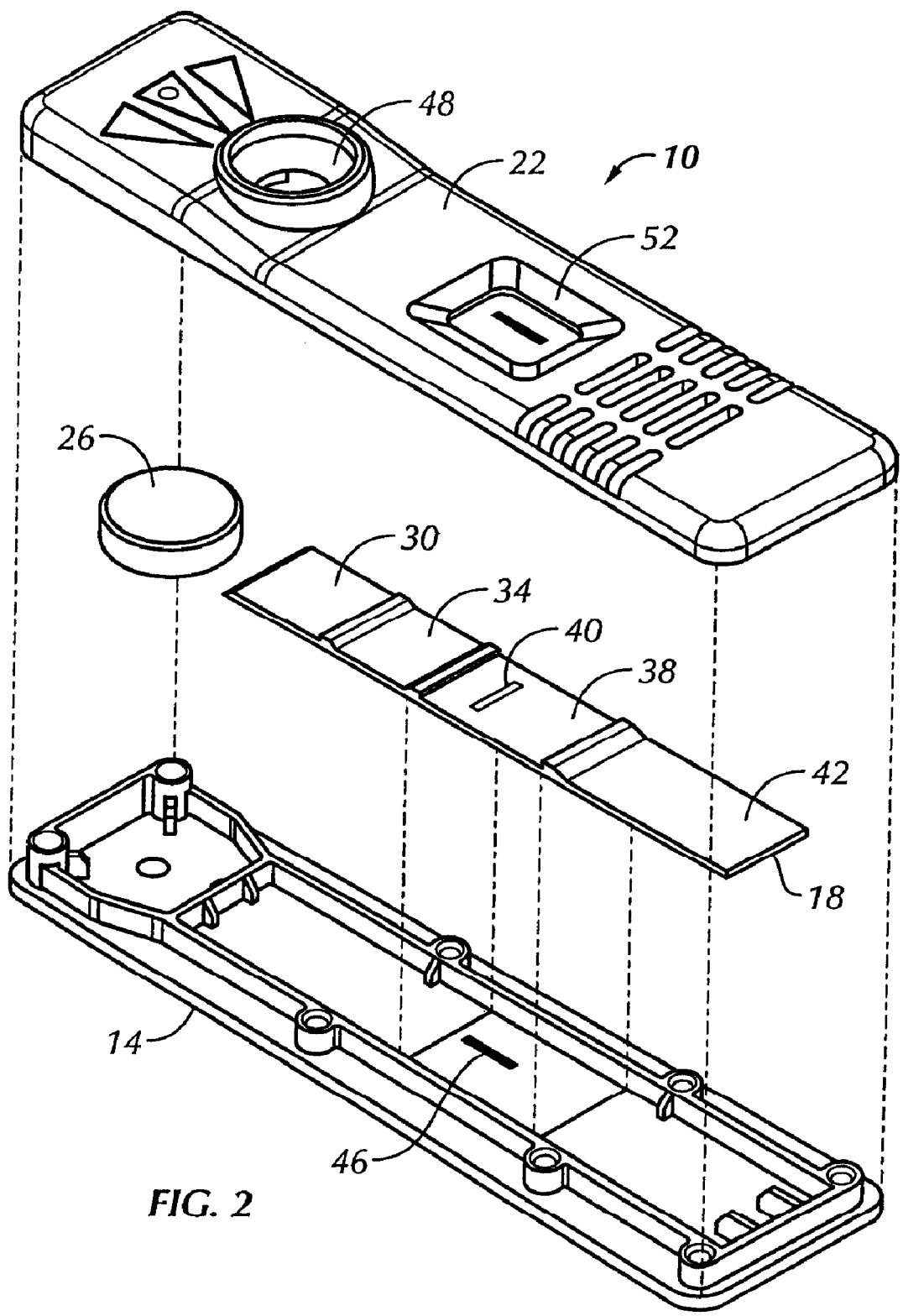
FIG. 2 is an exploded perspective view of a test device of the present invention showing a negative test result.

FIG. 2 illustrates the test device of the present invention showing a negative test result, in the instance where the fluid sample does not contain the analyte of interest.

In operation, the sample fluid is added through aperture 48, and on to application pad 30. The fluid sample is transported from application pad 30 to label zone 34, where the fluid is allowed to react with labeled reagent. Labeled reagent then binds with any analyte of interest contained in the fluid sample.

Next, the fluid sample is advanced to observation area 38, and then on to the absorbent zone. Observation area 38, now moistened by the sample fluid, becomes transparent. Consequently, mark 46 becomes visible through observation port 52. Through the observation port, the user can then view the mark displayed on the bottom support.

As shown here, there is no analyte present, and consequently no label is bound at capture zone 40. The resulting signal as manifested through observation port 52 is therefore in the shape of a minus (−) sign.

Figure 3:
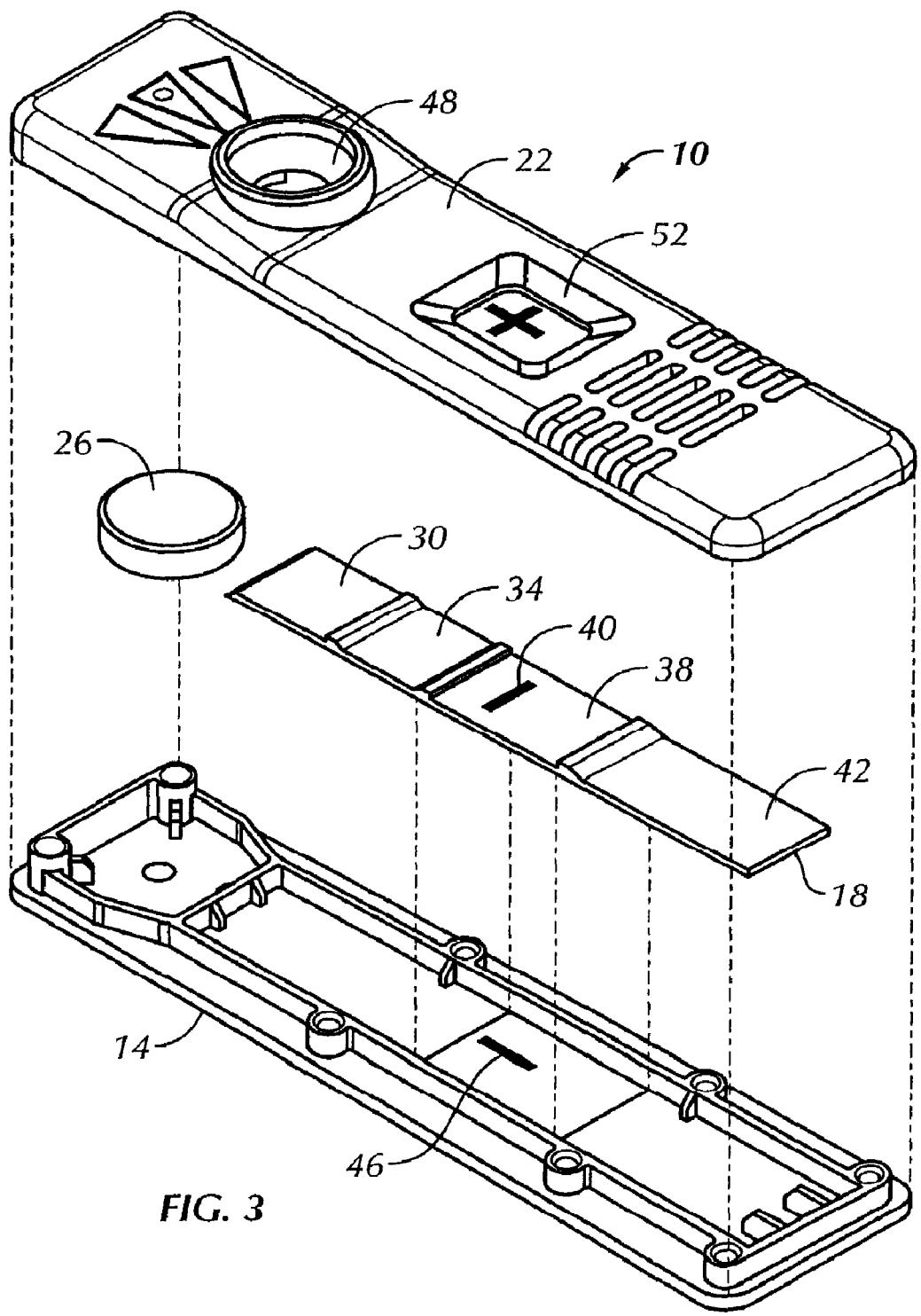
FIG. 3 is an exploded perspective view of a test device of the present invention showing a positive test result.

FIG. 3 illustrates the test device of the present invention showing a positive test result, in the instance where the fluid sample contains the analyte of interest.

In operation, the sample fluid is added through aperture 48, and on to application pad 30. The fluid sample is transported from application pad 30 to label zone 34, where the fluid is allowed to react with labeled reagent. Labeled reagent then binds with the analyte of interest contained in the fluid sample. Next, the fluid sample is advanced to observation area 38, and labeled analyte is restrained by capture reagent immobilized in capture zone 40. Unbound material in the fluid sample continues to flow into absorbent zone 42.

Observation area 38, now moistened by the sample fluid, becomes transparent. Consequently, mark 46 becomes visible through observation port 52. Through the observation port, the user can then view the mark displayed on the bottom support, in concert with the signal provided by the label contained in the capture zone. The resulting signal as manifested through observation port 52 is in the shape of a plus (+) sign.

Figure 4:
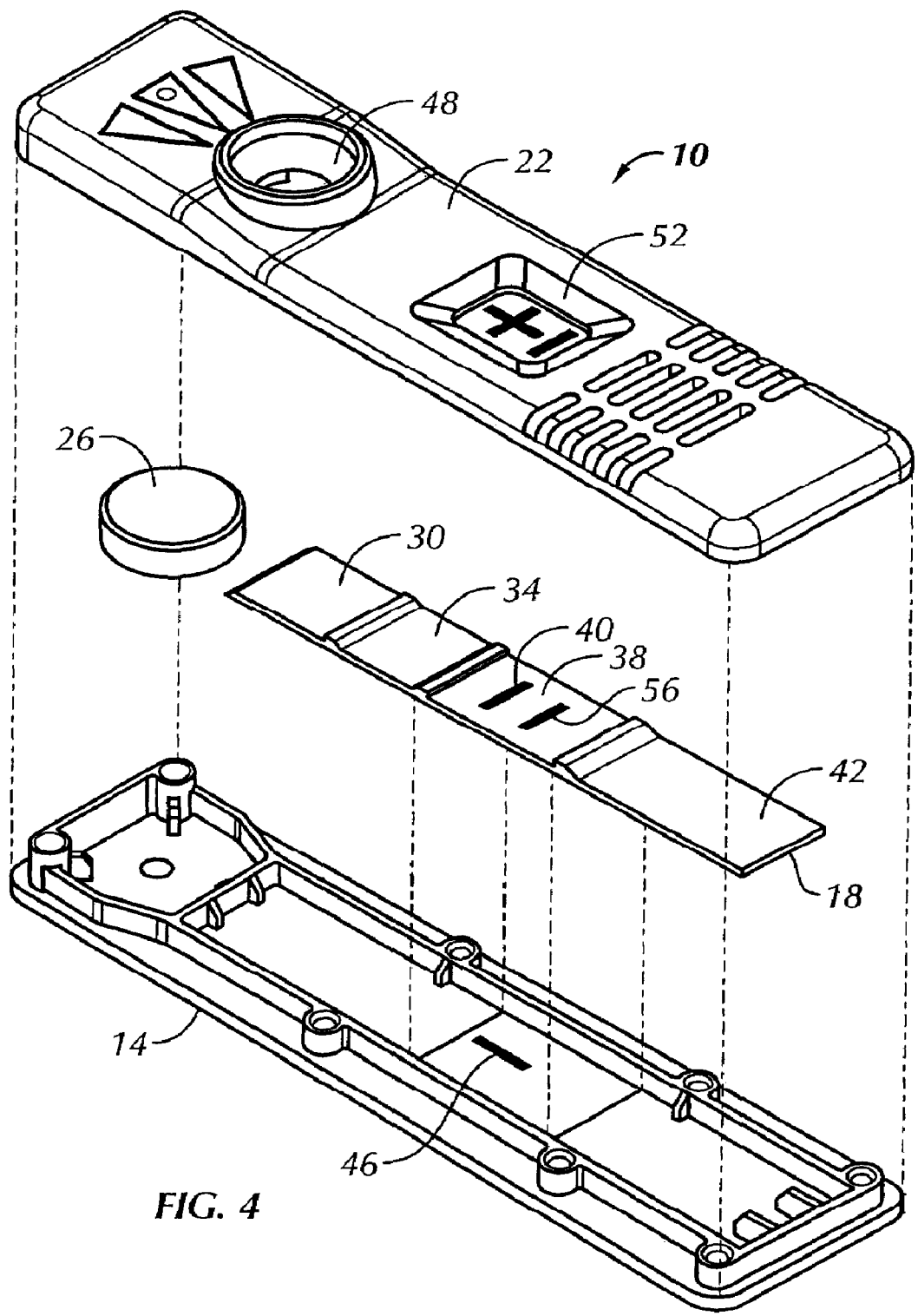
FIG. 4 is an exploded perspective view of a test device of the present invention showing a positive test result, and a procedural control line.

FIG. 4 shows the test device of the present invention, where observation area 38 further includes a procedural control line 56 that develops with any fluid sample flow, whether or not analyte is present in the sample.

The invention can be better understood by way of the following example which is representative of the preferred embodiment, but is not to be construed as limiting the scope of the invention.

EXAMPLES

Example 1

A lateral flow test device was constructed according to principles of the present invention. The test device included a G-III plastic bottom (#Z0846500), a G-III plastic scanner top (#Z0440900), a sample pad containing stock assay reagent, a label pad containing stock assay reagent, an observation zone as described below, and an absorbent pad (#0841000).

A nitrocellulose web assembly membrane from Millipore, trade name Highflow Plus Membrane, was combined with a clear Mylar backing.

A dark line was made on the inside of the plastic bottom, positioned parallel to sample flow in approximately the same area as would be underneath the fixed minus line from a current assay strip.

This bottom was then assembled with an experimental G-IV assay strip as described above, and a plastic scanner top. When a liquid sample was added to the test unit, the dark line, which was barely visible through the dry strip, became clearly visible. The results are shown generally in FIG. 2.

Example 2

Goat anti-alpha hCG antibodies were immobilized on Hiflow plus nitrocellulose membrane (nitrocellulose membrane cast on a transparent nylon sheet), manufactured by Millipore Inc. A second, unrelated protein was immobilized on the membrane for the procedural control line. The membrane was then blocked with a protein solution and dried prior to assembly.

A sample pad (non-woven rayon fiber backed with mylar) was impregnated with a buffered protein solutions and dried.

The label pad (non-woven rayon fiber backed with mylar) was impregnated with a solution containing red colored polystyrene microspheres coated with anti-beta hCG monoclonal antibodies, blue colored polystyrene microspheres coated with a binding pair member to the control line protein, and stabilizing agents followed by a drying process.

The sample and label pad, the capture membrane and an absorbent pad were then assembled into a test strip similar to FIG. 4.

A visible line was printed onto the bottom half of the plastic housing of a test cassette. The line was placed directly beneath and perpendicular to the immobilized goat anti-alpha hCG test line on the capture membrane. The preprinted line was approximately 1 mm thick and 5-9 mm long. The assembled test strip was then placed on top of the preprinted line into the bottom of the plastic housing as indicated in FIGS. 1-4, and the cassette was closed with the top portion of the plastic housing. Upon assembly, the preprinted line on the plastic housing was nearly invisible.

Upon addition of a liquid sample, the sample pad and label pad were re-hydrated and the sample wet the nitrocellulose capture membrane thus making it transparent. The preprinted line which was barely visible in the dry state was now clearly visible. The results are shown generally in FIG. 4.

What is claimed is:

1. A test device for determining the presence or absence of an analyte in a fluid sample, the test device comprising a test strip comprising, in fluid-flow contact with one another:
   a) a sample receiving zone for receiving a fluid sample,
   b) a label zone, comprising a label reagent that recognizes an analyte of interest, and
   c) a capture zone, comprising an immobilized capture reagent that binds directly or indirectly to the analyte,
   wherein the capture zone comprises a material that is opaque in the dry state and becomes transparent when moistened by the fluid sample and wherein said capture zone is visible during operation of the test device,
   the device further comprises a strip underlying the test stripe having a mark visible through the capture zone when moistened.

2. The test device of claim 1, wherein the capture zone further comprises an immobilized capture reagent.

3. The test device of claim 2, wherein the capture reagent is immobilized in the shape of a line.

4. The test device of claim 3, wherein the longitudinal axis of the line of capture reagent is in the direction of sample flow.

5. The test device of claim 1, further comprising a housing.

6. The test device of claim 1 wherein the strip underlying the test strip comprises Mylar.

7. The test device of claim 1, wherein the mark on the strip underlying the test strip is not visible prior to application of the fluid sample to the test device and becomes visible after application of the fluid sample to the device.

8. The test device of claim 1, wherein the mark is in the shape of a line, the longitudinal axis of which is perpendicular to sample flow.

9. The test device of claim 1, further comprising a control zone in fluid communication with the capture zone.

10. The test device of claim 9, wherein the control zone is visible during operation of the test device.

* * * * *